(12) United States Patent
Hayashi et al.

(10) Patent No.: US 10,010,490 B2
(45) Date of Patent: Jul. 3, 2018

(54) COSMETIC COMPOSITION COMPRISING CELLULOSE FIBERS WITH SMALL FIBER DIAMETER AND COMPARATIVELY SMALL ASPECT RATIO

(71) Applicant: NISSAN CHEMICAL INDUSTRIES, LTD., Tokyo (JP)

(72) Inventors: Hisato Hayashi, Funabashi (JP); Takehisa Iwama, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/649,614

(22) PCT Filed: Dec. 4, 2013

(86) PCT No.: PCT/JP2013/082597
§ 371 (c)(1),
(2) Date: Jun. 4, 2015

(87) PCT Pub. No.: WO2014/088034
PCT Pub. Date: Jun. 12, 2014

(65) Prior Publication Data
US 2015/0297469 A1 Oct. 22, 2015

(30) Foreign Application Priority Data

Dec. 4, 2012 (JP) ................................. 2012-265530

(51) Int. Cl.
| | | |
|---|---|---|
| *A61K 8/73* | (2006.01) | |
| *A61K 8/06* | (2006.01) | |
| *A61K 8/34* | (2006.01) | |
| *A61K 8/55* | (2006.01) | |
| *A61K 8/97* | (2017.01) | |
| *A61Q 19/00* | (2006.01) | |
| *A61K 8/02* | (2006.01) | |

(52) U.S. Cl.
CPC ............ *A61K 8/027* (2013.01); *A61K 8/0229* (2013.01); *A61K 8/06* (2013.01); *A61K 8/34* (2013.01); *A61K 8/345* (2013.01); *A61K 8/55* (2013.01); *A61K 8/73* (2013.01); *A61K 8/731* (2013.01); *A61K 8/97* (2013.01); *A61Q 19/00* (2013.01); *A61K 2800/10* (2013.01); *A61K 2800/262* (2013.01); *A61K 2800/412* (2013.01); *A61K 2800/48* (2013.01)

(58) Field of Classification Search
CPC .................................................. C08J 2301/02
See application file for complete search history.

(56) References Cited

U.S. PATENT DOCUMENTS

| | | | | | |
|---|---|---|---|---|---|
| 5,753,241 | A | * | 5/1998 | Ribier | .................... A61K 8/062 424/401 |
| 6,543,071 | B1 | | 4/2003 | Lenner | |
| 2012/0135505 | A1 | * | 5/2012 | Frangioni | ............ A61K 9/2054 435/277 |
| 2013/0122071 | A1 | * | 5/2013 | Cathala | ............... B01F 17/0028 424/401 |

FOREIGN PATENT DOCUMENTS

| | | | | | |
|---|---|---|---|---|---|
| CN | | 1284321 | A | 2/2001 | |
| CN | | 1331966 | A | 1/2002 | |
| DE | 10 2007 054702 | A1 | | 5/2009 | |
| EP | | 1582551 | A1 | 10/2005 | |
| EP | | 2526922 | A1 | 11/2012 | |
| EP | | 2 990 028 | A1 | 3/2016 | |
| JP | | 2913514 | B2 | 6/1999 | |
| JP | | 2001-002523 | A | 1/2001 | |
| JP | | 2008-050376 | A | 3/2008 | |
| JP | | 2009062332 | A | * 3/2009 | |
| JP | | 2010-037199 | A | 2/2010 | |
| JP | | 2010037200 | A | * 2/2010 | |
| JP | | 5002433 | B2 | 8/2012 | |
| JP | | 2012-193139 | A | 10/2012 | |
| WO | | 2010/106981 | A1 | 9/2010 | |
| WO | WO 2012017160 | A1 | * 2/2012 | ......... B01F 17/0028 | |
| WO | WO 2012156880 | A1 | * 11/2012 | ............. B01D 61/56 | |

OTHER PUBLICATIONS

Dumitriu, Polysaccharides: Structural Diversity and Functional Versatility, 2nd ed. pp. 46-53 (2004).*
J-PlatPat machine translation of Sekiguchi et al. (detailed description) downloaded Aug. 26, 2015.*
Park et al., Biotechnology for Biofuels, 3: 10 (2010).*
EPO translation of Isogai et al. , JP, 2010-037200, pub. Feb. 18, 2010, accessed on Apr. 4, 2016.*
EPO translation of Sakanishi et al., JP, 2012-193139, pub. Nov. 10, 2012, accessed on Mar. 30, 2016.*
Zugenmaier, Chp. 5, Crystalline Cellulose and Derivatives, Springer-Verlag Berlin Heidelberg (2008) pp. 101-174.*
Gea et al., Bioresource Technology, 102: 9105-9110 (2011).*
Bercea et al., American Chemical Society, 33: 6011-6016 (Year: 2002).*
Sacui et al., Aplied Materials & Interfaces, 6: 6127-6138 (Year: 2014).*
By Kalashnikova et al., Biomacromolecules, 13: 267-275, epub (Year: 2011).*

(Continued)

*Primary Examiner* — Bethany P Barham
*Assistant Examiner* — Lisbeth C. Robinson
(74) *Attorney, Agent, or Firm* — Oliff PLC

(57) ABSTRACT

There is provided a cosmetic additive in which the cosmetic obtained by mixing has excellent transparency, and good spread and feeling of use during application, and stickiness when dried can be suppressed, and a cosmetic containing the additive. A cosmetic additive containing cellulose fibers having an average fiber diameter (D) of 0.001 to 0.05 μm, and a ratio (L/D) of average fiber length (L) to average fiber diameter (D) of 5 to 500; and a cosmetic containing the cosmetic additive.

13 Claims, No Drawings

(56) References Cited

OTHER PUBLICATIONS

Urena benavides, Esteban, "Cellulose Nanocrystals Properties and Applications in Renewable Nanocomposites" All dissertations. Paper 704 (Year: 2011).*
Nov. 3, 2014 English Translation of Written Opinion issued in International Patent Application No. PCT/JP2013/082597.
Mar. 11, 2014 Search Report issued in International Patent Application No. PCT/JP2013/082597.
May 11, 2016 extended European Search Report issued in European Application No. 13861247.8.
Jan. 3, 2017 Office Action issued in Chinese Patent Application No. 201380071887.7.
Jun. 30, 2017 search report issued in European Application No. 13861247.8.
Fragrance Journal, 2007, No. 7, pp. 78-84.

* cited by examiner

COSMETIC COMPOSITION COMPRISING CELLULOSE FIBERS WITH SMALL FIBER DIAMETER AND COMPARATIVELY SMALL ASPECT RATIO

TECHNICAL FIELD

The present invention relates to a cosmetic additive containing cellulose fibers, and in particular, relates to a cosmetic additive containing cellulose fibers having small fiber diameter and comparatively small aspect ratio (that is, the fiber length is relatively short), and a polyhydric alcohol, and a cosmetic containing the same.

BACKGROUND ART

A cosmetic has various forms such as liquid, emulsion, gel, cream, stick, or the like. Various thickeners and gelators are used to improve the feeling of use and maintain properties of a product. Conventionally, examples of aqueous thickening and gelling agent for cosmetics may include water-soluble polymers including a natural polymer such as sodium hyaluronate, sodium alginate, and xanthan gum, a semisynthetic polymer such as hydroxyethyl cellulose and carboxymethyl cellulose, and a synthetic polymer such as a carboxyvinyl polymer, a polyvinyl alcohol, and polysodium acrylate. The thickening and gelling agent is appropriately selected from these and used depending on the purpose and the effect.

However, many thickening and gelling agents for cosmetics including a carboxyvinyl polymer that is mainly used are ionic. Therefore, the thickening and gelling agents have such problems that the viscosity of a cosmetic rapidly decreases due to an electrolyte such as sweats during application of the cosmetic to the skin, to slide down the cosmetic from the skin, and the cosmetic is unlikely to be applied due to the electrolyte. In order to solve such problems, an attempt to enhance the salt resistance and impart excellent feeling of use is made. For example, an aqueous gel cosmetic containing a carboxyvinyl polymer, a basic substance, a hydrophobic silicic anhydride, and a polyhydric alcohol (e.g., Patent Document 1) and the like have been proposed.

Further, in order to suppress stickiness during application, improve the feeling of use, and impart spray properties, an aqueous medium that is gelled by a low-molecular gelator is tried to be used as a cosmetic base material (Patent Document 2). The low-molecular gelator self-assembles to form a fiber form, resulting in a network structure, and the network structure encloses the aqueous medium and the like to form a gel. The gel is used for the cosmetic base material. Therefore, the gel can be immediately converted into a sol with adequate stress applied to the gel (cosmetic base material), to impart the spray properties to a cosmetic. Since the low-molecular gelator is not dissolved (molecules are not dispersed) in the aqueous medium, the feeling of use during application to the skin is improved. This is because an increase in viscosity of a solution and adherence when dried is suppressed to reduce stickiness and clumping.

Moreover, a gel cosmetic containing a low-crystalline regenerated cellulose obtained by a treatment with sulfuric acid, plant-derived oils, and a nonionic surfactant (Patent Document 3) has been proposed. Patent Document 3 describes that in order to achieve thixotropy in which the gel cosmetic can be sprayed in a mist form, cellulose fine particles having an average degree of polymerization of 100 or less, a fraction of cellulose I type crystal component of 0.1 or less, and a fraction of cellulose II type crystal component of 0.4 or less are preferred.

Using a cosmetic containing cellulose fibers obtained from plant-derived cellulose without a chemical treatment and a polyhydric alcohol, increased moisture retention and reduced stickiness are attempted (Patent Document 4).

PRIOR ART DOCUMENT

Patent Documents

Patent Document 1: Japanese Patent No. 2913514
Patent Document 2: International Publication WO 2010/106981 Pamphlet
Patent Document 3: Japanese Patent No. 5002433
Patent Document 4: Japanese Patent Application Publication No. 2012-193139 (JP 2012-193139 A)

SUMMARY OF THE INVENTION

Problem to be Solved by the Invention

As described above, various thickening and gelling agents for cosmetics have been proposed in an attempt to improve the performance, the feeling of use, and the like. For example, the aqueous gel cosmetic described in Patent Document 1 does not satisfy desired physical properties for a cosmetic, such as stickiness during application and application properties.

The gel cosmetic of Patent Document 3 using cellulose derived from low-crystalline regenerated cellulose obtained by a treatment with sulfuric acid has problems. For example, a complex procedure such as mixing of another component and use of a special stirrer for dilution is required, the heat resistance is low, the dispersibility is deteriorated by mixing an ionic component, the cosmetic becomes clouded, a precipitate is produced, and the cosmetic is separated.

In the cosmetic of Patent Document 4 using cellulose fibers obtained without a chemical treatment, the cellulose fibers have high aspect ratio (L/D) and a fiber length as very long as several tens to several thousands micrometers. Therefore, the cosmetic has problems in complex mixing and feeling of use. For example, the transparency is deteriorated by mixing the fibers in the cosmetic, and the skin dryness and clumping are caused by the fibers themselves when they are used alone, and therefore another component needs to be mixed.

An object of the present invention is to provide a cosmetic additive that exerts a thickening and gelling effect to solve the problems. Specifically, the object of the present invention is to provide a cosmetic additive in which the salt resistance and the heat resistance as properties conventionally desired for a cosmetic additive are excellent, mixing in a cosmetic is possible without a complex procedure, a cosmetic obtained by mixing can be sprayed in a mist form and cannot drip, and the dispersion stability is excellent even when an ionic compound is mixed, and in particular, a cosmetic additive in which the cosmetic obtained by mixing has excellent transparency, and good spread and feeling of use during application, and stickiness when dried can be suppressed, and a cosmetic containing the same.

Means for Solving the Problem

The present inventors have intensively investigated to solve the above-described problems, and as a result, found that in a dispersion containing cellulose fibers obtained by a refining process of high-pressure pulverization without a chemical treatment, and when a polyhydric alcohol is further added to the dispersion, cellulose fibers are not dissolved in a medium but are highly dispersed, the salt resistance, the heat resistance, as well as the transparency are excellent, the feeling of use to the skin is good, stickiness when dried can be suppressed, and the dispersion acts as an emulsion stabilizer. Thus, the present invention has been completed.

As a first aspect, the present invention relates to a cosmetic additive containing cellulose fibers having an average fiber diameter (D) of 0.001 to 0.05 μm, and a ratio (L/D) of an average fiber length (L) to an average fiber diameter (D) of 5 to 500.

As a second aspect, the present invention relates to the cosmetic additive according to the first aspect, further comprising a polyhydric alcohol, in addition to the cellulose fibers.

As a third aspect, the present invention relates to the cosmetic additive according to the second aspect, wherein the polyhydric alcohol is one or more selected from the group consisting of 1,3-butylene glycol, glycerol, and diglycerol.

As a fourth aspect, the present invention relates to the cosmetic additive according to the second or the third aspect, wherein the polyhydric alcohol is contained in an amount of 1 part by mass to 100 parts by mass relative to 1 part by mass of the cellulose fibers.

As a fifth aspect, the present invention relates to the cosmetic additive according to any one of the first to fourth aspects, wherein the cellulose fibers have a cellulose I type crystal structure.

As a sixth aspect, the present invention relates to the cosmetic additive according to the fifth aspect, wherein the cellulose fibers have only a cellulose I type crystal structure.

As a seventh aspect, the present invention relates to the cosmetic additive according to any one of the first to sixth aspects which is an additive to be added to increase viscosity of a cosmetic.

As an eighth aspect, the present invention relates to the cosmetic additive according to any one of the first to seventh aspects which is an additive to be added to a cosmetic for a cosmetic product that is used by spraying the cosmetic.

As a ninth aspect, the present invention relates to a cosmetic containing the cosmetic additive according to any one of the first to eighth aspects.

As a tenth aspect, the present invention relates to the cosmetic according to the ninth aspect, further comprising an aqueous component.

As an eleventh aspect, the present invention relates to the cosmetic according to the ninth or tenth aspect, further comprising an oil component.

As a twelfth aspect, the present invention relates to the cosmetic according to the eleventh aspect which has an emulsion form.

As a thirteenth aspect, the present invention relates to the cosmetic according to the ninth or tenth aspect, further comprising a surfactant.

As a fourteenth aspect, the present invention relates to the cosmetic according to the ninth or tenth aspect, further comprising an ionic compound.

As a fifteenth aspect, the present invention relates to an external preparation containing the cosmetic additive according to any one of the first to eighth aspects.

Effects of the Invention

The present invention can provide a cosmetic additive containing cellulose fibers that has excellent heat resistance and salt resistance, particularly excellent transparency and feeling of use to the skin, does not deposit an agglomerate or drip even when an oil component or an ionic component is mixed, and can suppress stickiness when dried and can be sprayed in a mist form, and a cosmetic containing the same.

MODES FOR CARRYING OUT THE INVENTION

A cosmetic additive of the present invention has main characteristics in which cellulose fibers refined by high-pressure pulverization without a chemical treatment are used, a polyhydric alcohol and a component such as an oil component and an ionic component can be mixed by a simple method.

In particular, in the cosmetic additive of the present invention and a cosmetic containing the same, cellulose fibers having an aspect ratio (L/D) as comparatively short as 5 to 500, as compared with conventionally proposed cellulose fibers, are used. Therefore, the cosmetic additive and the cosmetic especially have excellent transparency when they are mixed, and have characteristics in which the spread and the feeling of use during application are good. Further, the salt resistance and the heat resistance are excellent, dripping does not occur, and stickiness when dried is suppressed. Even when an ionic component is contained, the dispersion stability is excellent, and spraying in a mist form can be carried out. Hereinafter, the present invention will be described in detail.

<Cosmetic Additive>

[Cellulose Raw Material]

As a raw material for cellulose fibers used in the cosmetic additive of the present invention, for example, plant-derived cellulose such as wood, bamboo, hemp, jute, kenaf, cotton, field crop, and saburra, or cellulose produced by microorganisms or animals, such as bacterial cellulose, Cladophora, Glaucophyte (Glaucocystis), Valonia, and Hoya cellulose can be used.

In plant-derived cellulose, very fine fibers referred to as microfibrils form bundles, and fibrils, lamellae, and fiber cells are formed stepwise as higher order structures. In bacterial cellulose, cellulose microtibrils secreted from mycetocytes form a fine network structure as the diameter remains the same.

A crystalline material of naturally-occurring cellulose such as the plant-derived cellulose and the cellulose produced by microorganisms or animals is composed of a cellulose I type crystal, and the degree of crystallinity thereof largely varies depending on a cellulose source. The plant-derived cellulose forms a higher order structure containing impurities such as hemicellulose and lignin. Therefore, purified pulp obtained from the plant-derived cellulose as a raw material has a degree of crystallinity of about 50%. In contrast, purified pulp obtained from Cladophora, bacterial cellulose, Glaucocystis, or Hoya has as high degree of crystallinity as 80% or more.

In the present invention, high-purity cellulose raw material such as cotton and bacterial cellulose may be used as it is. It is preferable that the plant-derived cellulose other than the cellulose be isolated or purified before use.

It is preferable that the raw material for cellulose fibers used in the cosmetic additive of the present invention be cotton, bacterial cellulose, kraft pulp, or microcrystalline cellulose.

[Method for Pulverizing Cellulose]

In the present invention, cellulose fibers obtained by pulverizing the cellulose raw material are used. A method for pulverizing the cellulose raw material is not limited. In order to make the cellulose raw material finer to that with a fiber diameter and a fiber length that satisfy the object of the present invention, as described below, a method of generating high shear force, such as a media agitating mill including a high-pressure homogenizer, a grinder (stone mill), and a bead mill is preferred.

Among these, it is preferable that a high-pressure homogenizer be used for refinement. For example, refinement (pulverization) using a wet pulverization method described by Japanese Patent Application Publication No. 2005-270891 (JP 2005-270891 A) is desired. Specifically, a dispersion in which the cellulose raw material is dispersed is sprayed at high pressure from each of a pair of nozzles and collided to pulverize the cellulose raw material. For example, the refinement can be carried out using Star Burst system (high-pressure pulverization device manufactured by Sugino Machine Limited).

When the cellulose raw material is refined (pulverized) using the high-pressure homogenizer, the degrees of refinement and homogenization depend on the pressure at which the cellulose raw material is pressure-fed to a very high-pressure chamber of the high-pressure homogenizer, the number of times that the cellulose raw material is allowed to pass through the very high-pressure chamber (processing times), and the concentration of cellulose in an aqueous dispersion.

The pressure-feeding pressure (processing pressure) is usually 50 to 250 MPa, and preferably 150 to 245 MPa. A pressure-feeding pressure of less than 50 MPa does not sufficiently achieve refinement of cellulose, and an expected effect by the refinement is not obtained.

The concentration of cellulose in the aqueous dispersion during a refining process is 0.1% by mass to 30% by mass, and preferably 1% by mass to 10% by mass. When the concentration of cellulose in the aqueous dispersion is less than 0.1% by mass, the productivity is remarkably low, and when it is higher than 30% by mass, the pulverization efficiency is low, and desired cellulose fibers are not obtained.

The number of processing times for refinement (pulverization) is not particularly limited, and depends on the concentration of cellulose in the aqueous dispersion. When the cellulose concentration is 0.1 to 1% by mass, the number of processing times is about 10 to 100 to achieve sufficient refinement. When it is 1 to 10% by mass, the number of processing times needs to be about 10 to 1,000. When it is higher than 30% by mass, the number of processing times needs to be several thousands or more, and the viscosity increases to a viscosity at which the handling is difficult. Therefore, this is not realistic from the industrial viewpoint.

The average fiber diameter (D) of the cellulose fibers used in the present invention is 0.001 to 0.05 μm, and preferably 0.01 to 0.05 μm. Since cellulose fibers having an average fiber diameter of less than 0.001 μm is too thin, an addition effect is not obtained, that is, the properties of a cosmetic containing the cellulose fibers are not improved. Cellulose fibers having an average fiber diameter of more than 0.05 μm are not sufficiently pulverized. When the cellulose fibers are mixed in a cosmetic, the transparency is deteriorated, precipitation and aggregation are likely to occur in the cosmetic, and an expected effect such as improvement in spray properties and feeling of use is not obtained.

The aspect ratio (L/D) of the cellulose fibers used in the present invention is obtained as a ratio of average fiber length/average fiber diameter, and is 5 to 500, preferably 10 to 500, and the most preferably 20 to 110. When the aspect ratio is less than 5, the dispersibility of the fibers in a liquid is insufficient, and the coating property when dried is not sufficiently achieved. An aspect ratio of more than 500 means that the fiber length is extremely large. This decreases the transparency, and leads to degradation in the feeling of transparency and the feeling of use during application to the skin, and occurrence of clumping.

In the present invention, the average fiber diameter (D) of cellulose is determined as follows. A collodion-support film manufactured by Okenshoji Co., Ltd., is first subjected to a hydrophilic treatment for 3 minutes using an ion cleaner (JIC-410) manufactured by JEOL Ltd., and several droplets of cellulose dispersion (diluted with ultra pure water) produced in Production Example are added on the film, and dried at room temperature. This film is observed at an accelerating voltage of 200 kV with a transmission electron microscope (TEM, H-8000) (10,000-fold) manufactured by Hitachi, Lid. From a resulting image, the fiber diameters of 200 to 250 cellulose fibers as samples are each measured, and the average thereof is determined as the average fiber diameter (D).

For the average fiber length (L), the cellulose dispersion produced in Production Example is diluted 400 times by volume with dimethyl sulfoxide (DMSO) to disperse cellulose, and is casted on a silicon wafer in which the surface is subjected to a hydrophilic treatment using concentrated sulfuric acid in advance, and dried at 110° C. for 1 hour, to prepare a sample. This sample is observed with a scanning electron microscope (SEM, JSM-7400F) (10,000-fold) manufactured by JEOL Ltd. From a resulting image, the fiber lengths of 150 to 250 cellulose fibers as samples are each measured, and the average thereof is determined as the average fiber length (L).

[Polyhydric Alcohol]

A polyhydric alcohol usable in the present invention is not particularly limited. Examples thereof may include ethylene glycol, diethylene glycol, triethylene glycol, polyethylene glycol (weight-average molecular weight: 1,500 or less), trimethylene glycol, propylene glycol, dipropylene glycol, polypropylene glycol (weight-average molecular weight 1,500 or less), glycerol, diglycerol, triglycerol, polyglycerol having a degree of polymerization of more than 3, 1,3-butanediol, 3-methyl-1,3-butanediol, 1,3-butylene glycol, 1,3-propanediol, 1,2-pentanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, 1,2-octanediol, 1,2-decanediol, 1,2-dodecanediol, 1,2-tetradecanediol, 1,2-hexadecanediol, 1,2-octadecanediol, and trimethylolpropane. In the present invention, it is preferable that one of them may be used or two or more of them may be used in combination.

Among these, it is preferable that 1,3-butylene glycol, glycerol, or diglycerol be used.

The polyhydric alcohol is desirably used in an amount of 1 part by mass to 100 parts by mass, and preferably 1 part by mass to 20 parts by mass, relative to 1 part by mass of the cellulose fibers.

The cosmetic additive of the present invention is suitable as an additive to be added to increase the viscosity of a cosmetic, that is, an additive for thickening.

Further, the cosmetic additive of the present invention is suitable as an additive to be added to a cosmetic for a cosmetic product that is used by spraying the cosmetic, that is, an additive for a spray cosmetic. When the cosmetic additive is added, a cosmetic spray having excellent spraying performance in which spreading of spray is excellent and liquid dripping is improved can be formed.

<Cosmetic>

The present invention also provides a cosmetic containing the cosmetic additive. The cosmetic can contain an aqueous component, an oil component, a surfactant, an electrolyte, and the like.

The cosmetic of the present invention may have various forms such as a skin lotion (lotion), an emulsion, a cream, and a gel.

The present invention also provides an external preparation containing the cosmetic additive, and the external preparation can contain various components that are the same as those of the cosmetic.

[Aqueous Component]

As the aqueous component, water, alcohol, or a mixed solvent of water and alcohol may be used. Water and a mixed solvent of water and alcohol are more preferred, and water is further preferred.

The water is not particularly limited as long as it can be usually used for a cosmetic product. Examples thereof may include deionized water, pure water, purified water, natural water, hot spring water, deep-sea water, and steam-distilled water (aromatic distilled water) obtained by steam distillation of plant and the like.

The alcohol is preferably a water-soluble alcohol that is freely dissolved in water, more preferably a $C_{1-6}$ alcohol, further preferably methanol, ethanol, 2-propanol, or i-butanol, and particularly preferably ethanol or 2-propanol.

[Oil Component]

An oil component usable in the cosmetic of the present invention is not particularly limited. Examples thereof may include plant-derived oils and fats such as olive oil, jojoba oil, castor oil, soybean oil, rice oil, rice germ oil, coconut oil, palm oil, cocoa oil, meadowfoam oil, shea butter, tea tree oil, avocado oil, macadamia nut oil, and olive squalane; animal-derived oils and fats such as squalane, minke whale oil, and turtle oil; wax such as bees wax, carnauba wax, rice wax, and lanolin; hydrocarbons such as liquid paraffin, vaseline, and paraffin wax; fatty acids such as myristic acid, palmitic acid, stearic acid, oleic acid, isostearic acid, and cis-11-eicosenic acid; higher alcohols such as lauryl alcohol, cetanol, and stearyl alcohol; and synthetic esters and synthetic triglycerides such as isopropyl myristate, isopropyl palmitate, butyl oleate, 2-ethylhexyl glyceride, and an octyldodecyl ester of higher fatty acid (octyldodecyl stearate).

The amount of the oil component to be mixed preferably falls within a range of 0.01 to 99% by mass relative to the total amount of the cosmetic.

[Surfactant]

A surfactant usable in the cosmetic of the present invention is not particularly limited. Examples thereof may include anionic surfactants such as a fatty acid soap (sodium laurate, sodium palmitate, sodium stearate, etc.), potassium lauryl sulfate, and alkyl sulfuric acid triethanol amine ether; cationic surfactants such as stearyltrimethylammonium chloride, benzalkonium chloride, and lauryl amine oxide; amphoteric surfactants such as an imidazoline-based amphoteric surfactant (2-cocoyl-2-imidazolinium hydroxide-1-carboxyethyloxy-2-sodium salt, etc.), a betaine-based surfactant (alkyl betaine, amidobetaine, and sulfobetaine, etc.), and acyl methyltaurine; nonionic surfactants such as sorbitan fatty acid esters (sorbitan monostearate, sorbitan sesquioleate, etc.), glycerol fatty acids (glycerol monostearate, etc.), propylene glycol fatty acid esters (propylene glycol monostearate, etc.), a hydrogenated castor oil derivative, glycerol alkyl ether, a sucrose fatty acid ester, and alkylglucoside; and polyoxyethylene surfactants such as a polyoxyethylene alkyl ether, a polyoxyethylene sorbitan fatty acid ester, a polyoxyethylene hydrogenated castor oil, a polyoxyethylene polyoxypropylene alkyl ether, and a polyoxyethylene sorbitol fatty acid ester.

The amount of the surfactant to be mixed preferably falls within a range of 0.01 to 20% by mass relative to the total amount of the cosmetic.

[Electrolyte]

An electrolyte may have a form of inorganic or organic salt, and is preferably water-soluble and non-irritating to the skin. Examples thereof may include electrolytes that can be mixed in an external preparation, or particularly in a cosmetic product, a drug for external use, or a quasi-drug.

The amount of the electrolyte to be mixed preferably falls within a range of 0.001 to 30% by mass relative to the total amount of the cosmetic.

Specific examples of the electrolyte may include an inorganic salt and an organic salt. Preferred examples of the electrolyte may include an inorganic salt such as sodium chloride, potassium chloride, calcium chloride, magnesium chloride, zinc chloride, aluminum chloride, calcium carbonate, sodium carbonate, potassium carbonate, magnesium carbonate, potassium sulfite, sodium sulfate, sodium hydrogen sulfate, sodium sulfite, sodium hydrogen sulfite, potassium sulfate, sodium sulfate, calcium sulfate, magnesium sulfate, zinc sulfate, aluminum sulfate, potassium phosphate, sodium phosphate, disodium hydrogen phosphate, and sodium dihydrogen phosphate; a glycyrrhizinate salt such as dipotassium glycyrrhizinate; a salt of α-hydroxy acid such as aminocaproic acid, citric acid, salicylic acid, lactic acid, glycolic acid, and tartaric acid; an amino acid such as serine, glycine, asparagine, aspartic acid, tranexamic acid, lysine, threonine, alanine, tyrosine, valine, leucine, proline, arginine, threonine, cysteine, cysteine, methionine, tryptophan, glutamic acid, and pyrrolidone carboxylic acid, and a derivative thereof; and vitamins such as ascorbic acid, sodium ascorbate, potassium ascorbate, magnesium ascorbate, sodium ascorbic acid ester, magnesium ascorbyl phosphate, calcium ascorbyl phosphate, sodium ascorbyl sulfate, magnesium ascorbyl sulfate, calcium ascorbyl sulfate, ascorbyl glucoside (2-0-α-D-glucopyranosyl-L-ascorbic acid), ascorbyl glucosamine, dehydroascorbic acid, vitamin B2, vitamin B6, vitamin B12, vitamin B13, biotin, pantothenic acid, niacin, folic acid, inositol, carnitine, thiamine, thiamine disulfide, fursultiamine, dicethiamine, bisbutytiamine, bisbentiamine, benfotiamine, thiamine monophosphate disulfide, cycotiamine, octotiamine, and prosultiamine. Further examples thereof may include disodium ethylenediaminetetracetate, trisodium ethylenediaminetetracetate, tetrasodium ethylenediaminetetracetate, sodium benzoate, 2-hydroxy-4-methoxybenzophenone-5-sulfonate salt, adenosine-3'-5'-cyclic monophosphate, adenosine monophosphate, adenosine diphosphate, adenosine triphosphate, and salts thereof.

Among these, sodium chloride, potassium chloride, calcium chloride, magnesium chloride, zinc chloride, aluminum chloride, sodium carbonate, potassium carbonate, potassium sulfite, sodium sulfate, sodium hydrogen sulfate, sodium sulfite, sodium hydrogen sulfite, potassium sulfate, calcium sulfate, magnesium sulfate, zinc sulfate, aluminum sulfate, potassium phosphate, sodium phosphate, disodium hydrogen phosphate, and sodium dihydrogen phosphate are further preferred.

In the present invention, water-soluble means that at least 0.1% by mass of substance can be dissolved in pure water at 25° C.

[Other Component]

In addition to the cellulose fibers and the polyhydric alcohol, a functional additive can be used as another component material for the cosmetic additive containing the cellulose fibers and the cosmetic containing the same of the present invention. Examples of the functional additive may include a moisturizer, a preservative, organic fine particles, inorganic fine particles, a deodorant, a perfume, an organic solvent, and a water-soluble polymer. The functional additive may be used singly or two or more thereof may be used in combination.

EXAMPLES

Hereinafter, characteristics of the present invention will be described more specifically with reference of Examples and Comparative Examples. Materials, amounts, ratios, treatments, and procedures shown in the following Examples can be optionally changed without departing from the spirit of the present invention. Therefore, the scope of the present invention should not be construed as being restricted to the following specific examples.

[Measurement of Average Fiber Diameter D and Average Fiber Length L]

In accordance with procedures described, the average fiber diameter D and the average fiber length L of cellulose fibers obtained in each of Production Examples 1 to 3 were measured from a TEM image and a SEM image. The aspect ratio L/D was determined from the average fiber diameter D and the average fiber length L.

[Measurement of Zeta Potential]

A dispersion in each of Production Examples 1 to 3 was filtered through a 0.45-μm membrane filter to produce a water-containing non-woven fabric sheet. A zeta potential in the produced sheet was measured in a 10 mM-NaCl aqueous solution in which monitoring particles for measurement of zeta potential were dispersed using a cell unit for plate measurement (ELS Z series manufactured by Otsuka Electronics Co., Ltd.).

Production Example 1

Production of Cellulose Fibers Derived from Microcrystalline Cellulose 1,000 parts by mass of pure water was added to 15 parts by mass of commercially available microcrystalline cellulose (FUNACEL powder II for column chromatography manufactured by Funakoshi Co., Ltd.) and the cellulose was dispersed. The dispersion was subjected to a pulverization treatment 300 times at 200 MPa using a high-pressure pulverization device (Star Burst system) manufactured by Sugino Machine Limited to obtain an aqueous dispersion (MC) of cellulose fibers derived from microcrystalline cellulose. The obtained dispersion was weighed and placed in a dish, and dried at 110° C. for 5 hours to remove moisture content. The amount of the residue was measured, and the concentration was measured. The concentration of cellulose (solid content concentration) in water was 1.2% by mass.

Production Example 2

Production of Cellulose Fibers Derived from Pulp 478.3 parts by mass of pure water was added to 21.7 parts by mass of commercially available kraft pulp (LBKP D-8 manufactured by Kokusai Pulp & Paper Co., Ltd., solids content: 46% by mass) and the kraft pulp was dispersed. The dispersion was subjected to a pulverization treatment 280 times at 245 MPa using a high-pressure pulverization device (Star Burst system) manufactured by Sugino Machine Limited to obtain an aqueous dispersion (PC) of cellulose fibers derived from pulp. The obtained dispersion was weighed and placed in a dish, and dried at 110° C. for 5 hours to remove moisture content. The amount of the residue was measured, and the concentration was measured. The concentration of cellulose (solid content concentration) in water was 1.5% by mass.

Production Example 3

Production of Cellulose Fibers Derived from Bacterial Cellulose

686 Parts by mass of commercially available bacterial cellulose (PT. NIRAMAS manufactured by UTAMA, solid content of cellulose in acetic acid aqueous solution: about 0.5% by mass) was pulverized using a mixer for domestic use. The resulting slurry was filtered, and dispersed in pure water, and the pH thereof was measured. The same operation was repeated until the pH was neutral (6 to 7). The resulting dispersion of bacterial cellulose was subjected to a pulverization treatment 30 times at 200 MPa using a high-pressure pulverization device (Star Burst system) manufactured by Sugino Machine Limited to obtain an aqueous dispersion (BC) of cellulose fibers derived from bacterial cellulose. The obtained dispersion was weighed and placed in a dish, and dried at 110° C. for 5 hours to remove moisture content. The amount of the residue was measured, and the concentration was measured. The concentration of cellulose (solid content concentration) in water was 0.4% by mass.

The average fiber diameter D, the average fiber length L, and the zeta potential of the cellulose fibers obtained in each of Production Examples 1 to 3 were measured in accordance with the procedures described above. The results and an aspect ratio (L/D) calculated from the average fiber diameter D, and the average fiber length L are shown.

TABLE 1

| | Average fiber diameter D [nm] | Average fiber length L [nm] | Aspect ratio L/D | Zeta potential [mV] |
|---|---|---|---|---|
| Production Example 1 (MC) | 24 | 594 | 24 | −35.4 |
| Production Example 2 (PC) | 19 | 1960 | 103 | −21.7 |
| Production Example 3 (BC) | 36 | 2470 | 69 | −11.8 |

Examples 1 to 7 and Comparative Examples 1 to 7

From the cellulose fibers prepared in each of Production Examples 1 to 3 and various thickening components, each evaluation liquid (cosmetic) in Examples and Comparative Examples was prepared.

The cellulose fibers, the thickening component (not added in Comparative Examples 1 and 2), a polyhydric alcohol, and ion-exchange water were mixed so that the composition was as shown in Table 2, and the mixture was stirred for 1 hour using a magnetic stirring bar and a magnetic stirrer to prepare an evaluation liquid. For a carboxyvinyl polymer (Comparative Example 4), a carboxyvinyl polymer that was dissolved in a polyhydric alcohol and ion-exchange water, and neutralized with a 0.1-N or 1.0-N sodium hydroxide aqueous solution was used as an evaluation liquid.

Appearance evaluation, sensory evaluation, and spray test shown below were carried out using each evaluation liquid (cosmetic) in Examples 1 to 7 and Comparative Examples 1 to 7. The obtained results are shown in Table 2 together.

[Appearance Evaluation]

Each evaluation liquid (cosmetic) in Examples 1 to 7 and Comparative Examples 1 to 7 was placed in a 20-mL transparent glass container, and the container was sealed and allowed to stand for one day. The dispersibility of the evaluation liquid was evaluated by visual decision in accordance with the following criteria.

<Evaluation Criteria>

Dispersibility ○: Precipitation and an insoluble substance are not observed.
Homogeneous solution or dispersion
  ×: Precipitation and an insoluble substance are observed.

[Sensory Evaluation]

In a room with constant temperature and humidity (25° C., 50% R. H.), the evaluation liquid in each of Examples and Comparative Examples was sprayed to the back of hand of four subjects three times using a spray vial (No. 2, manufactured by Maruemu Corporation) (in an amount of 0.1 g), and spread. In sensory evaluation, permeation into the skin and stickiness during application, occurrence of clumping after application, and dryness after drying were evaluated in accordance with the following evaluation criteria.

<Evaluation Criteria>

Permeation into the skin ⊙: Four subjects judged the evaluation liquid to have good permeation into the skin.
  ○: Three subjects judged the evaluation liquid to have good permeation into the skin.
  Δ: Two subjects judged the evaluation liquid to have good permeation into the skin.
  ×: Three or more subjects judged the evaluation liquid to have poor permeation into the skin.
Stickiness ⊙: Four subjects judged the evaluation liquid not to be sticky.
  ○: Three subjects judged the evaluation liquid not to be sticky.
  Δ: Two subjects judged the evaluation liquid not to be sticky.
  ×: Three subjects or more judged the evaluation liquid to be sticky.
Dryness ⊙: Four subjects judged the evaluation liquid to cause little fibrous clumping and no dryness.
  ○: Three subjects judged the evaluation liquid to cause little fibrous clumping and no dryness.
  Δ: Two subjects judged the evaluation liquid to cause clumping, but to cause little dryness.
  ×: Three subjects or more judged the evaluation liquid to cause dryness and much clumping.

[Spray Test]

Each evaluation liquid was sprayed to a glass substrate three times using a spray vial (No. 2, manufactured by Maruemu Corporation) at a distance of 3.5 cm, and spreading and liquid dripping of mist attached to the glass substrate were evaluated in accordance with the following evaluation criteria.

<Evaluation Criteria>

Mist spreading ○: Full-cone spray, diameter: 4 to 2 cm
  ×: Solid steam spray, diameter: less than 2 cm or non-sprayable
Liquid dripping ○: No liquid dripping
  ×: Liquid dripping was observed Each component used in Examples and Comparative Examples shown in Table 2 are as follows;

Cellulose fiber MC: cellulose fibers obtained in Production Example 1
Cellulose fiber PC: cellulose fibers obtained in Production Example 2
Cellulose fiber BC: cellulose fibers obtained in Production Example 3
Low-crsytalline cellulose: Cellodene 4M manufactured by DAI-ICHI KOGYO SEIYAKU CO., LTD. [cellulose particles: particle size distribution: 8 to 30 nm, particle diameter: 10 to 20 nm]
Carboxyvinyl polymer: Carbopol 940 manufactured by I.T.O. Co., Ltd.
Crystalline cellulose: CELGUM C-91 manufactured by Mingtai Chemical Co., Ltd.
[Microcrystalline Cellulose Coated with Sodium Carboxymethyl Cellulose (Microcrystalline Cellulose: 89%, Sodium Carboxymethyl Cellulose: 11%), 330-mesh Passage Ratio (45 μm): 55% or More]
Hydroxypropyl cellulose: HPC SSL manufactured by Nippon Soda Co., Ltd.
Hypromellose and methyl cellulose: METOLOSE 60SH-4000 manufactured by Shin-Etsu Chemical Co., Ltd. (in Tables, described as "hypromellose")
Glycerol: Glycerol manufactured by I.T.O. Co., Ltd.
1,3-BG: 1,3-butylene glycol manufactured by I.T.O. Co., Ltd.

TABLE 2

| | | Example | | | | | | | Comparative Example | | | | | | |
|---|---|---|---|---|---|---|---|---|---|---|---|---|---|---|---|
| | | 1 | 2 | 3 | 4 | 5 | 6 | 7 | 1 | 2 | 3 | 4 | 5 | 6 | 7 |
| Thickening component | Cellulose fibers MC | 1 | 1 | 1 | | | | | | | | | | | |
| | Cellulose fibers PC | | | | 1.4 | 1.4 | | | | | | | | | |
| | Cellulose fibers BC | | | | | | 0.3 | 0.3 | | | | | | | |
| | Low-crystalline cellulose | | | | | | | | | | 1.5 | | | | |
| | Carboxyvinyl polymer | | | | | | | | | | | 1 | | | |
| | Crystalline cellulose | | | | | | | | | | | | 1 | | |
| | Hydroxypropyl cellulose | | | | | | | | | | | | | 1 | |
| | Hypromellose | | | | | | | | | | | | | | 1 |
| Polyhydric alcohol | Glycerol | 5 | | | 5 | | 5 | | 5 | | | | | | |
| | 1,3-BG | | 5 | | | 5 | | 5 | | 5 | 5 | 5 | 5 | 5 | 5 |
| | Purified wafer | 99 | 94 | 94 | 98.6 | 93.6 | 99.7 | 94.7 | 95 | 95 | 93.5 | 94 | 94 | 94 | 94 |

TABLE 2-continued

| | | Example | | | | | | | Comparative Example | | | | | | |
|---|---|---|---|---|---|---|---|---|---|---|---|---|---|---|---|
| | | 1 | 2 | 3 | 4 | 5 | 6 | 7 | 1 | 2 | 3 | 4 | 5 | 6 | 7 |
| Appearance Spray | Dispersibility | ○ | ○ | ○ | ○ | ○ | ○ | ○ | ○ | ○ | X | ○ | X | ○ | ○ |
| | Mist spreading | ○ | ○ | ○ | ○ | ○ | ○ | ○ | ○ | ○ | ○ | X | | ○ | X |
| | Liquid dripping | ○ | ○ | ○ | ○ | ○ | ○ | ○ | X | X | X | X | | X | X |
| Sensory evaluation | Permeation into the skin | ○ | ◎ | ◎ | ○ | ◎ | ○ | ◎ | Δ | Δ | ○ | ○ | ○ | ○ | Δ |
| | Stickiness | ○ | ○ | ○ | ◎ | ○ | ○ | ○ | Δ | Δ | Δ | X | Δ | Δ | X |
| | Dryness | ◎ | ◎ | ◎ | ○ | ○ | Δ | ○ | ○ | ○ | ○ | Δ | ○ | ○ | Δ |

Example 8 and Comparative Examples 8 to 12

An evaluation liquid (cosmetic) having a composition shown in Table 3 in each of Example 8 and Comparative Examples 8 to 12 was prepared.

Egg yolk lecithin was added to olive oil so that the composition was as shown in Table 3, and the mixture was stirred and dispersed using a magnetic stirring bar and a magnetic stirrer. After then, 1,3-butylene glycol, the cellulose fibers produced in Production Example 2 as an emulsion stabilizer component, and ion-exchange water were added to the mixture, and the mixture was stirred for 1 hour to prepare an emulsified evaluation liquid. In Comparison Examples, each evaluation liquid was prepared in the same manner as in Examples using each emulsion stabilizer component described in Comparative Examples 8 to 12 of Table 3. For a carboxyvinyl polymer (Comparative Example 11), a carboxyvinyl polymer that was dissolved and neutralized with a 1.0-N sodium hydroxide aqueous solution was used.

Appearance evaluation of emulsion liquid shown below and the spray test were carried out using each evaluation liquid (cosmetic) in Example 8 and Comparative Examples 8 to 12. The obtained results are shown in Table 3 together.

[Appearance Evaluation of Emulsion Liquid]

Each evaluation liquid in Example 8 and Comparative Examples 8 to 12 was placed in a 20-mL transparent glass container, and the container was sealed. The homogeneity of the evaluation liquid when the container was sealed and the stability with time (homogeneity) after storage at 50° C. in a constant temperature bath for one week were evaluated by visual decision in accordance with the following criteria.

<Evaluation Criteria>
Homogeneity ○: Appearance is not changed at all, and oil float and separation are not observed.
  Δ: Oil float and separation are slightly recognized.
  ×: Oil float and separation are clearly recognized.

Each component used in Table 3 is as follows:
Olive oil: JUNSEI CHEMICAL CO., LTD., Japanese Standards of Quasi-drug Ingredients, olive oil
Egg yolk lecithin: Kewpie Corporation, egg yolk lecithin PL-30S
1,3-BG: 1,3-butylene glycol manufactured by I.T.O. Co., Ltd.
Cellulose fiber PC: cellulose fibers obtained in Production Example 2
Low-crsytalline cellulose: Cellodene 4M manufactured by DAI-ICHI KOGYO SEIYAKU CO., LTD.
Carboxyvinyl polymer: Carbopol 940 manufactured by I.T.O. Co., Ltd.
Xanthan gum: KETROL CG-SFT manufactured by Sansho Co., Ltd.

TABLE 3

| | | Example | Comparative Example | | | | |
|---|---|---|---|---|---|---|---|
| | | 8 | 8 | 9 | 10 | 11 | 12 |
| Oils | Olive oil | 20 | 20 | 20 | 20 | 20 | 20 |
| Emulsifier | Egg yolk lecithin | 1 | 1 | | 1 | 1 | 1 |
| Polyhydric alcohol | 1,3-BG | 5 | 5 | 5 | 5 | 5 | 5 |
| Emulsion stabilizer | Cellulose fibers PC | 1 | | 1 | | | |
| | Low-crystalline cellulose | | | | 1.5 | | |
| | Carboxyvinyl polymer | | | | | 0.1 | |
| | Xanthan gum | | | | | | 0.7 |
| Pure water | | 73 | 74 | 74 | 73 | 73.9 | 73.3 |
| Total amount | | 100 | 100 | 100 | 100 | 100 | 100 |
| Appearance evaluation of emulsion liquid | Homogeneity | ○ | x | x | ○ | ○ | ○ |
| | Stability with time (at 50° C. after 1 week) | ○ | x | x | x | ○ | x |
| Spray properties | Mist spreading | ○ | — | — | ○ | x | x |
| | Liquid dripping | ○ | — | — | ○ | ○ | x |

As apparent from the results shown in Table 2, in Examples 1 to 7 using the cellulose fibers of the present invention as the thickening component, the dispersibility, the spray properties, and the feeling of use are excellent. In contrast, in Comparative Examples 3 and 5 using the low-crystalline cellulose (shape: particles, crystal structure: mixture of I type and II type) and the crystalline cellulose (shape: powder with a size larger than the cellulose fibers of the present invention, crystal structure: I type), respectively, as the thickening component, results of deteriorated dispersibility and spray properties are obtained. In Comparative Examples 4, 6, and 7 using a carboxyvinyl polymer, hydroxypropyl cellulose, and hypromellose, respectively, as the water-soluble thickener, liquid dripping during spraying is confirmed, and results of stickiness when dried and poor feeling of use are obtained As apparent from the results shown in Table 3, in Example 8 using the cellulose fibers of the present invention, the dispersibility and the stability of the emulsion liquid are improved and the spray properties are also good. The reason for improving the dispersibility and the stability of the emulsion liquid is considered that fibers in the emulsion are tangled to form a three-dimensional network. In Comparative Examples 11 and 12 using a carboxyvinyl polymer and xanthan gum, respectively, that are generally used as the emulsion stabilizer, results of low homogeneity and low spray properties are obtained.

INDUSTRIAL APPLICABILITY

The cellulose cosmetic additive and the cosmetic containing the same of the present invention are different from a conventional water-soluble thickener, can be sprayed, have good permeation into the skin, suppress stickiness and dryness even when dried, and have excellent feeling of use. Further, the cellulose cosmetic additive and the cosmetic that exert excellent action of an emulsion stabilizer, have excellent stability with time and good spray properties can be provided, and an external preparation, a skin protectant, and a wound dressing that have excellent feeling of use can he provided.

The invention claimed is:

1. A cosmetic containing a cosmetic additive consisting of cellulose fibers having an average fiber diameter (D) of 0.001 to 0.036 μm, and a ratio (L/D) of average fiber length (L) to average fiber diameter (D) of 5 to 500, and a polyhydric alcohol, wherein the cellulose fibers consist essentially of cellulose fibers derived from microcrystalline cellulose as the only cellulose fibers having a crystal structure, the polyhydric alcohol is one or more selected from the group consisting of 1,3-butylene glycol, glycerol, and diglycerol, and the cosmetic contains no water-soluble polymer.

2. The cosmetic according to claim 1, wherein the polyhydric alcohol is contained in an amount of 1 part by mass to 100 parts by mass relative to 1 part by mass of the cellulose fibers.

3. The cosmetic according to claim 1, wherein the cellulose fibers have an average fiber diameter (D) of 0.01 to 0.036 μm.

4. The cosmetic according to claim 1, wherein the cellulose fibers have a ratio (L/D) of average fiber length (L) to average fiber diameter (D) of 10 to 500.

5. The cosmetic according to claim 1, wherein the cellulose fibers have a ratio (L/D) of average fiber length (L) to average fiber diameter (D) of 20 to 110.

6. The cosmetic according to claim 1, wherein the cellulose fibers have an average fiber diameter (D) of 0.019 to 0.036 μm and a ratio (L/D) of average fiber length (L) of 20 to 110.

7. The cosmetic according to claim 1, which is a liquid and contains the additive in an amount effective to increase the viscosity of the cosmetic in the absence of said additive.

8. The cosmetic according to claim 1, further comprising an aqueous component.

9. The cosmetic according to claim 1, further comprising an oil component.

10. The cosmetic according to claim 9 which has an emulsion form.

11. The cosmetic according to claim 1, further comprising a surfactant.

12. The cosmetic according to claim 1, further comprising an ionic compound.

13. An external preparation containing the cosmetic according to claim 1.

* * * * *